US010813766B2

(12) United States Patent
Xue et al.

(10) Patent No.: US 10,813,766 B2
(45) Date of Patent: Oct. 27, 2020

(54) METHODS OF MANUFACTURING AND DESIGNING A LIGHTWEIGHT FEMORAL STEM FOR HIP IMPLANTS

(71) Applicant: ZSFab, Inc., Cambridge, MA (US)

(72) Inventors: Zhenyu Xue, Somerville, MA (US); Kai Xu, Somerville, MA (US); Jing Zhang, Somerville, MA (US)

(73) Assignee: ZSFab, Inc., Cambridge, MA (US)

( * ) Notice: Subject to any disclaimer, the term of this patent is extended or adjusted under 35 U.S.C. 154(b) by 48 days.

(21) Appl. No.: 16/359,178

(22) Filed: Mar. 20, 2019

(65) Prior Publication Data
US 2019/0321185 A1    Oct. 24, 2019

Related U.S. Application Data

(62) Division of application No. 16/114,730, filed on Aug. 28, 2018, now Pat. No. 10,278,823.
(Continued)

(51) Int. Cl.
*A61F 2/36* (2006.01)
*A61F 2/30* (2006.01)
*A61L 27/56* (2006.01)

(52) U.S. Cl.
CPC ............ *A61F 2/3676* (2013.01); *A61F 2/367* (2013.01); *A61F 2/3662* (2013.01);
(Continued)

(58) Field of Classification Search
CPC ...... A61F 2/3662; A61F 2/367; A61F 2/3672; A61F 2/3676; A61F 2/30767;
(Continued)

(56) References Cited

U.S. PATENT DOCUMENTS

| 4,938,771 A | 7/1990 | Vecsei et al. |
| 5,133,767 A | 7/1992 | Frey et al. |

(Continued)

FOREIGN PATENT DOCUMENTS

| DE | 3743329 C1 | 6/1989 |
| FR | 2194123 A5 | 2/1974 |
| WO | WO-2015164982 A1 * 11/2015 ........... A61L 27/365 |

OTHER PUBLICATIONS

Lawrence E. Murr, et al., "Next-generation biomedical implants using additive manufacturing of complex, cellular and functional mesh arrays," Phil. Trans. R. Soc. A (2010) 368, 1999-2032, doi:10.1098/rsta.2010.0010.
(Continued)

*Primary Examiner* — David H Willse
*Assistant Examiner* — Javier G Blanco
(74) *Attorney, Agent, or Firm* — American Patent Agency PC; Daniar Hussain; Xiaomeng Shi

(57) ABSTRACT

A method of manufacturing a femoral stem for a hip implant includes forming a femoral neck extending from a proximal end of the femoral stem towards a distal end of the femoral stem, forming an upper section connected to and extending from the femoral neck towards the distal end of the femoral stem, and forming a lower section connected to and extending from the upper section to the distal end of the femoral stem. Further, a method for designing a femoral stem for a hip implant includes generating a customized femoral stem model to match an information of a patient, generating at least one proximal-distal solid rib in the upper section, calculating density and stress distributions for an open lattice and for a closed lattice, and selecting a unit cell type and a pore size for the open lattice and the closed lattice to match a density and/or a stiffness of the patient's femur.

7 Claims, 13 Drawing Sheets

Related U.S. Application Data

(60) Provisional application No. 62/659,440, filed on Apr. 18, 2018.

(52) U.S. Cl.
CPC ......... *A61F 2/30767* (2013.01); *A61F 2/3672* (2013.01); *A61F 2002/30011* (2013.01); *A61F 2002/3092* (2013.01); *A61F 2002/30593* (2013.01); *A61F 2002/30602* (2013.01); *A61F 2002/30879* (2013.01); *A61F 2002/30962* (2013.01); *A61F 2002/368* (2013.01); *A61F 2002/3678* (2013.01); *A61L 27/56* (2013.01)

(58) Field of Classification Search
CPC ........ A61F 2002/368; A61F 2002/3092; A61F 2002/30593; A61F 2002/30602; A61F 2002/30879; A61F 2002/30962; A61F 2002/3678; A61L 27/56; B33Y 10/00; B33Y 80/00
See application file for complete search history.

(56) References Cited

U.S. PATENT DOCUMENTS

| | | | |
|---|---|---|---|
| 6,685,987 | B2 | 2/2004 | Shetty |
| 8,828,311 | B2 | 9/2014 | Medina et al. |
| 2004/0243246 | A1 | 12/2004 | Lyren |
| 2010/0042226 | A1 | 2/2010 | Nebosky et al. |
| 2012/0064288 | A1* | 3/2012 | Nakano ............... A61L 27/06 428/117 |
| 2014/0363481 | A1 | 12/2014 | Pasini et al. |
| 2017/0095337 | A1 | 4/2017 | Pasini et al. |

OTHER PUBLICATIONS

Lawrence E. Murr, et al., "Next Generation Orthopaedic Implants by Additive Manufacturing Using Electron Beam Melting," International Journal of Biomaterials, vol. 2012, Article ID 245727, doi:10.1155/2012/245727.

Bruno Jette, et al., "Femoral stem incorporating a diamond cubic lattice structure: Design,manufacture and testing," Journal of the Mechanical Behavior of Biomedical Materials, 77 (2018), 58-72, doi:10.1016/j.jmbbm.2017.08.034.

Ghiba M. Ovidiu, et al., "Influence of the Lattice Structures on the Mechanical Behavior of Hip Endoprostheses," 2010 Advanced Technologies for Enhancing Quality of Life, 2010 IEEE, doi:10.1109/ATEQUAL.2010.16.

Sajad Arabnedjad, et al., "Fully Porous 3D Printed Titanium Femoral Stem to Reduce Stress-Shielding Following Total Hip Arthroplasty," J Orthop Res 35:1774-1783, 2017, doi:10.1002/jor.23445.

Yingjun Wang, et al., "Lattice Hip Implant Design by Multi-Scale Multi-Constraint Topology Optimization," XXIV ICTAM, Aug. 21-26, 2016, Montreal, Canada.

Brad J. Farrell, et al., "An animal model to evaluate skin-implant-bone integration and gait with a prosthesis directly attached to the residual limb," Clinical Biomechanics 29 (2014) 336-349, doi:10.1016/j.clinbiomech.2013.12.014.

DePuy Synthes Joint Reconstruction, A Johnson & Johnson Company, "Corail Hip System," 2013, U.S.

Sajad Arabnejad, et al., "Fully Porous 3D Printed Titanium Femoral Stem to Reduce Stress-Shielding Following Total Hip Arthroplasty," J Orthopaedic Research, 2016, doi:10.1002/jor.23445.

Dalia Mahmoud, et al., "Lattice Structures and Functionally Graded Materials Applications in Additive Manufacturing of Orthopedic Implants: A Review," J. Manuf. Mater. Process. 1 (13), 2017, doi:10.3390/jmmp1020013.

* cited by examiner

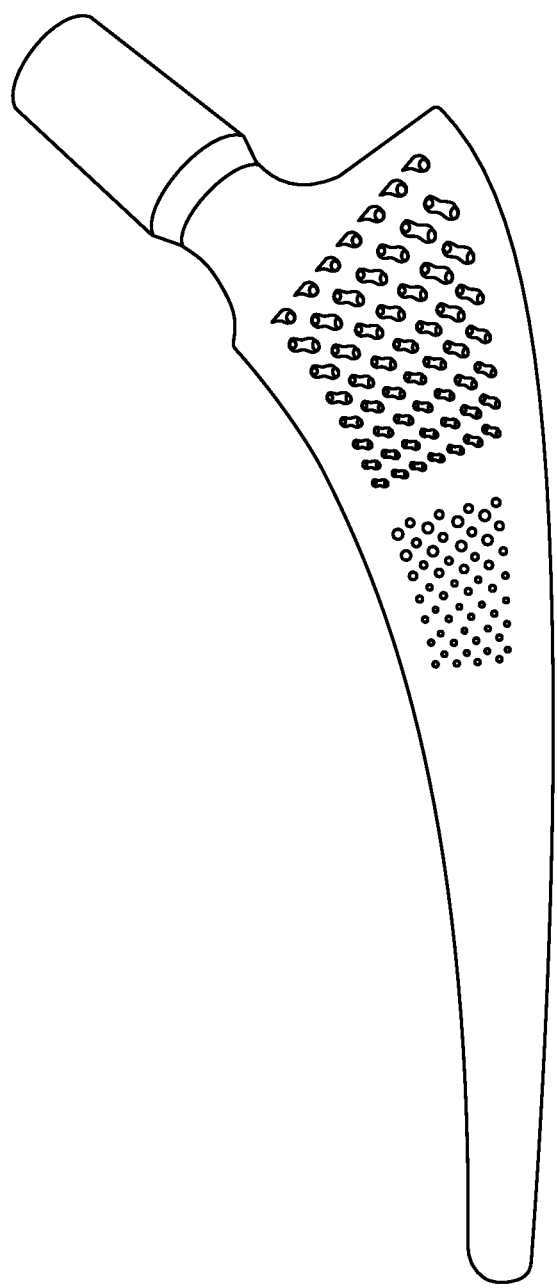
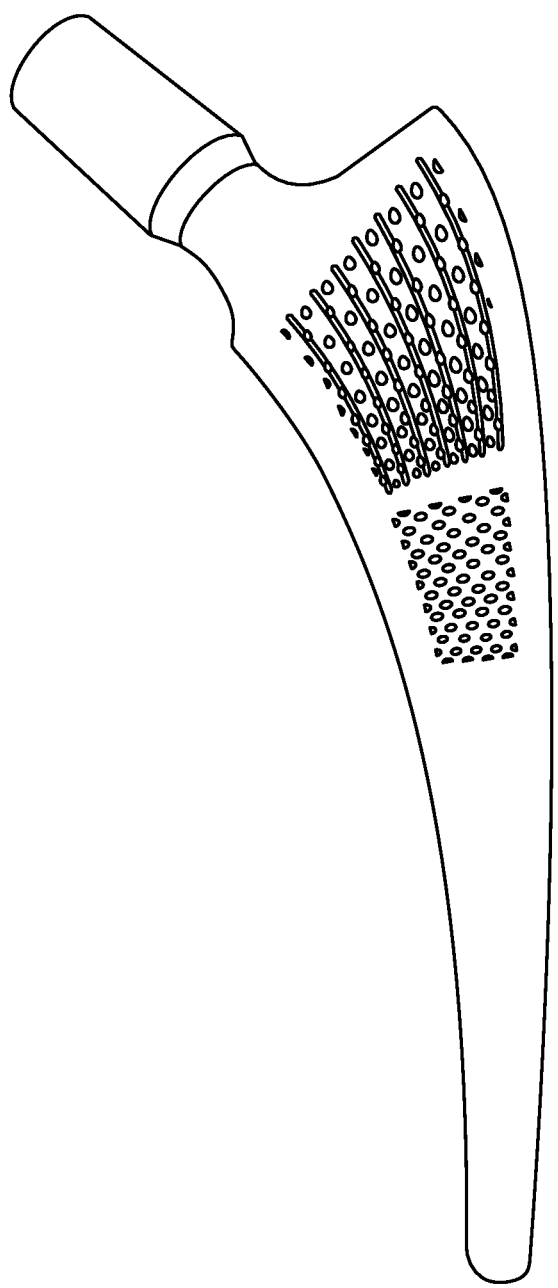
*FIG. 4*  *FIG. 5*

800
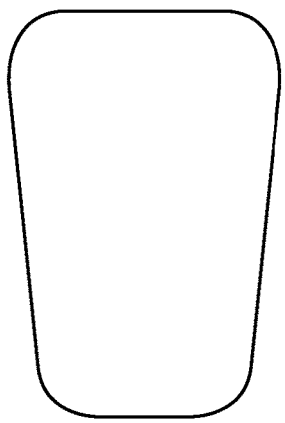
TRAPEZOID
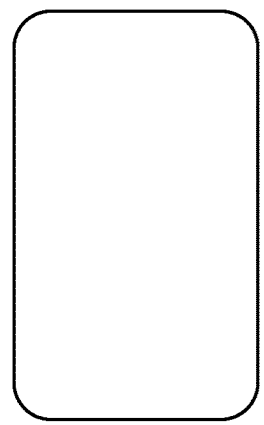
QUADRANGLE
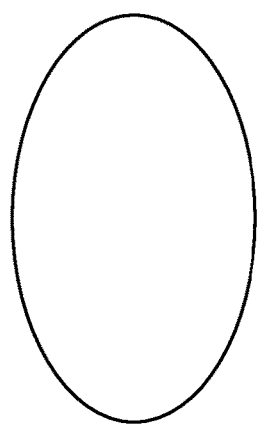
ELLIPSE
*FIG. 8*

METHODS OF MANUFACTURING AND DESIGNING A LIGHTWEIGHT FEMORAL STEM FOR HIP IMPLANTS

RELATED APPLICATIONS

This application is a divisional of and claims priority to U.S. Ser. No. 16/114,730, filed on 28 Aug. 2018, entitled "LIGHTWEIGHT FEMORAL STEM FOR HIP IMPLANTS," which itself is a non-provisional of and claims priority to U.S. Ser. No. 62/659,440, filed on 18 Apr. 2018, entitled "LIGHTWEIGHT FEMORAL STEM FOR HIP IMPLANTS," the entire disclosures of both of which are hereby incorporated by reference in their entireties herein.

NOTICE OF COPYRIGHTS AND TRADEDRESS

A portion of the disclosure of this patent document contains material which is subject to copyright protection. This patent document may show and/or describe matter which is or may become tradedress of the owner. The copyright and tradedress owner has no objection to the facsimile reproduction by anyone of the patent disclosure as it appears in the U.S. Patent and Trademark Office files or records, but otherwise reserves all copyright and tradedress rights whatsoever.

FIELD OF THE INVENTION

Embodiments of the present invention broadly relate to hip implants, and pertain particularly to methods and systems for customized manufacture and use of lightweight femoral stems for hip implants.

BACKGROUND OF THE INVENTION

The statements in this section may serve as a background to help understand the invention and its application and uses, but may not constitute prior art.

Hip replacement surgery such as total hip arthroplasty (total hip replacement, THR) and hemiarthroplasty is a surgical procedure commonly used to relieve pain, restore function, and improve the quality of life for patients with compromised hip joints when conservative treatments have failed. Despite its success, hip replacement surgery may also lead to complications such as aseptic loosening, stress shielding, and even periprosthetic fracture. Bone resorption secondary to stress shielding can also arise from the mismatch of the mechanical properties between the implant and the surrounding native femoral bone.

Although hip replacement implants have been used and greatly improved in their form and construction over the years, several issues still exist for conventional hip implant designs. First, conventional hip implants are prefabricated with several standard, fixed sizes. Doctors choose a best fitting implant according to patient's personal bone size and conditions. For example, the diameter of the femoral head and the size of the femoral stem are often estimated with preoperative planning, and further manually confirmed and fitted intraoperatively by testing the femoral head prosthesis within the acetabulum, and the femoral stem within the medullary canal based on cement usage. However, each person is different with unique bone anatomies, so very often a standard size does not match the patient's bone perfectly as desired. A poor fit reduces the longevity of device, leading to device failures and harmful wear particles.

Second, existing hip implants are mostly made through casting and molding processes with solid metals such as chromium-cobalt alloy, the density of which is more than twice as that of natural bone. A heavier implant can cause discomfort and a reduced quality of life for the patient.

Third, current implant materials such as titanium-based alloys, chromium cobalt alloys, and 316L stainless steel have stiffness significantly higher than that of natural bone. Once a metal implant is secured in place, most of the physiological loading is transferred to the implant, with stress "shielded" away from the surrounding femur. As healthy bones constantly remodel in response to the load they are placed under, the load transfer in the implanted femur causes under-loading of the bone, leading to bone resorption and loss of bone mass. This phenomenon is termed as bone loss secondary to stress shielding. The reduction in bone stock can lead to serious complications, including peri-prosthetic fracture, while the mismatch in elastic modulus between the implant and the bone can result in thigh pain. Stress shielding also obstructs bone growth and reduces the quality of the remaining bone stock, leading to a significantly increased risk of fracture and aseptic loosening with revision surgery.

Therefore, in view of the aforementioned difficulties, there is an unsolved need for personalized hip implants and implant components with optimal weight and stiffness for faster bone growth, bone density matching, and enhanced fatigue strength.

It is against this background that various embodiments of the present invention were developed.

BRIEF SUMMARY OF THE INVENTION

Embodiments of the present invention provides a lightweight femoral stem for a hip implant with optimized stiffness, enhanced fatigue strength, and shape and size customized according to individual patients' needs. Embodiments of the present invention utilizes 3D printing to generate a femoral stem model with reinforcement designs and multiple sections with a combination of different lattice structures, capable of matching bone's natural density and stiffness, promoting faster bone growth in response to increased mechanical stimulation than conventional implants, and enhancing fatigue strength of hip implants. Three-dimensional (3D) printing techniques facilitates the manufacturing process and ensures consistent quality of the device.

More specifically, one embodiment of the present invention is a femoral stem for a hip implant, comprising a femoral neck extending from a proximal end of the femoral stem towards a distal end of the femoral stem; an upper section connected to and extending from the femoral neck towards the distal end of the femoral stem, wherein the upper section comprises at least one proximal-distal solid rib flanked by an open lattice; and a lower section connected to and extending from the upper section to the distal end of the femoral stem, wherein the lower section comprises a closed lattice enclosed in a solid skin.

In some embodiments of the present invention, the at least one solid rib comprises four or more proximal-distal solid ribs. In some embodiments of the present invention, the four or more proximal-distal solids ribs are pairs of parallel ribs In some embodiments of the present invention, the at least one proximal solid rib is selected from the group consisting of a plate in an anterior-posterior direction, a plate in a medial-lateral direction, and an intersection of two plates.

In some embodiments of the present invention, the upper section further comprises a transverse plate, wherein the transverse plate divides the open lattice into a first portion and a second portion. In some embodiments of the present invention, the first portion and the second portion are different in at least one of a unit cell type and a pore size.

In some embodiments of the present invention, each of the open lattice and the closed lattice comprises a unit cell selected from the group consisting of a truss lattice, a gyroid lattice, and a Schoen's I-WP lattice.

In some embodiments of the present invention, a pore size of the open lattice is smaller than a pore size of the closed lattice. In some embodiments of the present invention, the pore size of the open lattice is between 0.1 mm inclusive and 5 mm inclusive. In some embodiments of the present invention, the pore size of the closed lattice is larger than or equal to 2 mm.

In some embodiments of the present invention, the femoral neck is collared.

In some embodiments of the present invention, the femoral neck comprises a closed lattice. In some embodiments of the present invention, a top of the femoral neck comprises an escape hole. In some embodiments of the present invention, the femoral neck comprises a solid base plate that separates the femoral neck and the upper section.

In some embodiments of the present invention, the upper section and the lower section is separated by a solid transverse plate. In some embodiments of the present invention, the lower section comprises a bottom escape hole connected to the closed lattice.

In another aspect, another embodiment of the present invention is a method of manufacturing a femoral stem for a hip implant, comprising the steps of forming a femoral neck extending from a proximal end of the femoral stem towards a distal end of the femoral stem; forming an upper section connected to and extending from the femoral neck towards the distal end of the femoral stem, wherein the upper section comprises at least one proximal-distal solid rib flanked by an open lattice; and forming a lower section connected to and extending from the upper section to the distal end of the femoral stem, wherein the lower section comprises a closed lattice enclosed in a solid skin.

In some embodiments of the present invention, the at least one solid rib comprises four or more proximal-distal solid ribs. In some embodiments of the present invention, the upper section further comprises a transverse plate, wherein the transverse plate divides the open lattice into a first portion and a second portion. In some embodiments of the present invention, the first portion and the second portion are different in at least one of a unit cell type and a pore size. In some embodiments of the present invention, a pore size of the open lattice is smaller than a pore size of the closed lattice.

In yet another aspect, yet another embodiment of the present invention is a method for designing a femoral stem for a hip implant, comprising the steps of generating a customized femoral stem model to match an information of a patient, wherein the femoral stem model comprises a femoral neck extending from a proximal end of the femoral stem towards a distal end of the femoral stem, an upper section connected to and extending from the femoral neck towards the distal end of the femoral stem, and a lower section connected to and extending from the upper section to the distal end of the femoral stem; generating at least one proximal-distal solid rib in the upper section; calculating density and stress distributions for an open lattice flanking the at least one proximal-distal solid rib in the upper section, and for a closed lattice with the lower section; and selecting a first lattice unit cell type and a first pore size for the open lattice and a second lattice unit cell type and a second pore size for the closed lattice to match a density and/or a stiffness of the patient's femur.

In some embodiments of the present invention, the information of the patient comprises at least one of a femur shape, a size, a density, and a stiffness.

In some embodiments of the present invention, the at least one solid rib comprises four or more proximal-distal solid ribs. In some embodiments of the present invention, the upper section further comprises a transverse plate, wherein the transverse plate divides the open lattice into a first portion and a second portion.

In some embodiments of the present invention, the first portion and the second portion are different in at least one of a unit cell type and a pore size. In some embodiments of the present invention, the first pore size of the open lattice is smaller than the second pore size of the closed lattice.

Yet other aspects of the present invention include methods and processes comprising the steps described herein, and also include the processes and modes of operation of the systems, devices, and articles described herein. Other aspects and embodiments of the present invention will become apparent from the detailed description of the invention when read in conjunction with the attached drawings.

BRIEF DESCRIPTION OF THE DRAWINGS

Embodiments of the present invention described herein are exemplary, and not restrictive. Embodiments will now be described, by way of examples, with reference to the accompanying drawings. For purposes of clarity, not every component is labeled in every drawing. The drawings are not necessarily drawn to scale, with emphasis instead being placed on illustrating various aspects of the devices described herein.

FIGS. 4 and 5 are profile views of two femoral stem designs for a hip implant, respectively, illustrating different open lattices, according to some embodiments of the present invention.

FIG. 8 is a diagram showing illustrative transverse cross-sections of a femoral stem of a hip implant, according to several embodiments of the present invention

DETAILED DESCRIPTION OF THE INVENTION

Figure 1:
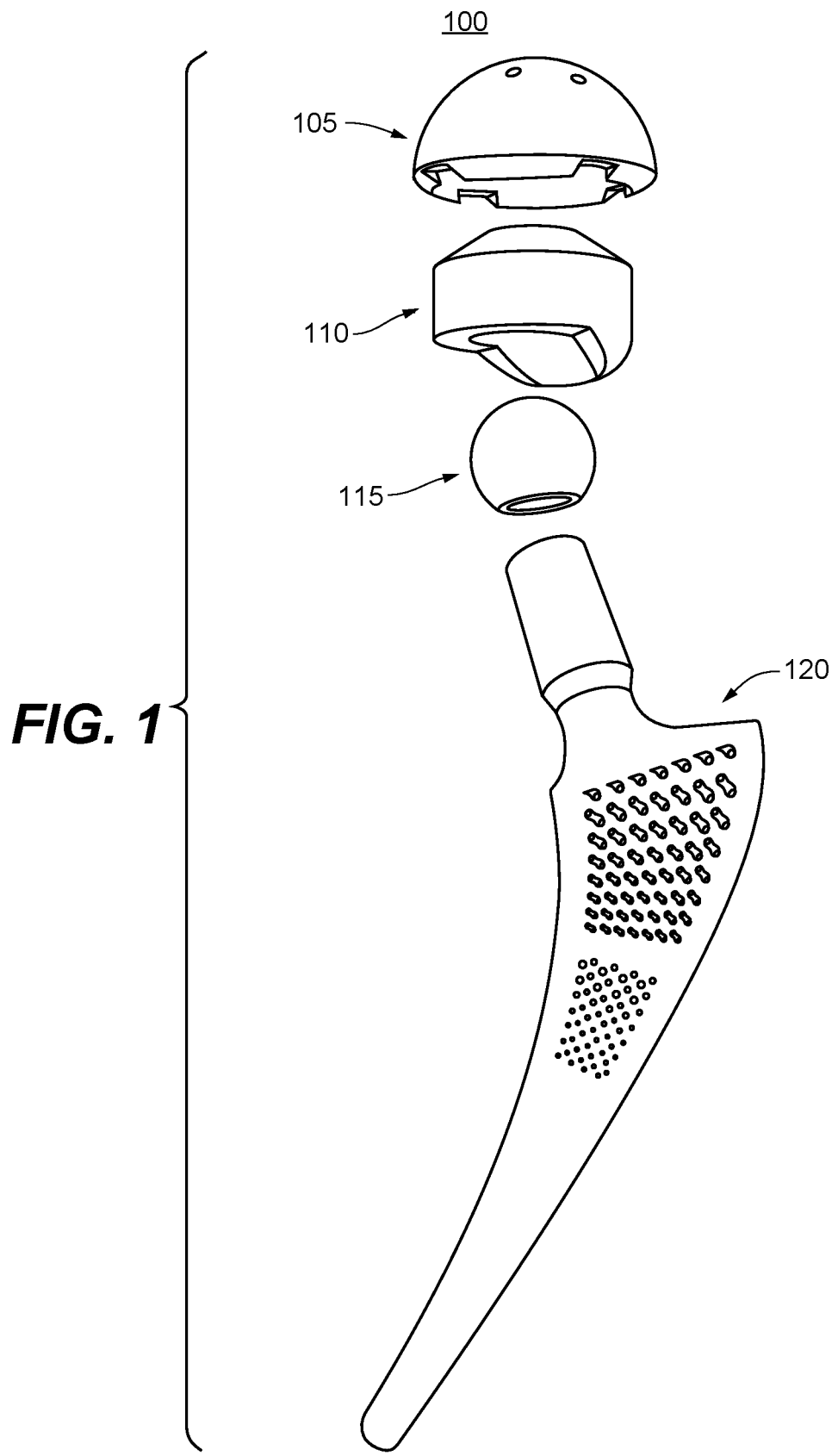
FIG. 1 is a schematic diagram for a modular hip implant assembly, according to one embodiment of the present invention.

In the following description, for purposes of explanation, numerous specific details are set forth in order to provide a thorough understanding of the invention. It will be apparent, however, to one skilled in the art that the invention can be practiced without these specific details. In other instances, structures, devices, processes, and methods are shown using schematics, use cases, and/or diagrams in order to avoid obscuring the invention. Although the following description contains many specifics for the purposes of illustration, anyone skilled in the art will appreciate that many variations and/or alterations to suggested details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

Broadly, embodiments of the present invention relate to orthopedic implants, methods and systems for manufacture, and particularly to femoral stem design of hip implants for total hip arthroplasty (total hip replacement, THR) and hemiarthroplasty. A THR replaces both the acetabulum and the femoral head, while hemiarthroplasty replaces only the femoral head.

Conventional manufacturing methods of hip implants uses casting or tooling to form solid implants which are heavy and may not provide a best fit to individual patients. More recently, 3D printing techniques such as Electron Beam Melting (EBM) and selective laser melting (SLM) have been adopted to manufacture hip implants, including both solid implant models for metal casting molding, and latticed implant models with customized lattice micro-structure in the middle section of the stem. Latticed femoral stem can accommodate bone ingrowth at the interface between the implant and the bone interior surface. Nonetheless, existing solid and latticed femoral stems are not optimized to match in stiffness and weight to patient's bone, with latticed micro-structures also often lead to poor fatigue strength for the hip implant.

By comparison, embodiments of the present invention feature a combined use of rib reinforcement design and multi-sectional lattice structures to match bone's natural density and stiffness, promoting faster bone growth in response to increased mechanical stimulation than stiffer implants, and enhancing fatigue strength of hip implant. Furthermore, the present design facilitates the use of 3D-printing technology in the manufacturing process to achieve individual customization of the implant and to ensure the quality of the final product. In short, embodiments of the present invention provide a shape-customized, lightweight femoral stem and hip implant design with optimized biomechanical performance, enhanced fatigue strength, and suitability for additive manufacturing.

FIG. 1 is a schematic diagram for a modular hip implant assembly 100, according to one embodiment of the present invention. Hip implant assembly 100 may be used for total hip replacement, and comprises an acetabular shell 105 for replacing the acetabulum, a polyethylene insert 110 to serve as a socket liner, a femoral head 115 to enable movement of the hip joint, and a femoral stem 120 for insertion and implant into the proximal femur. With modular prostheses, individualized combinations of femoral head, heck, and stem with different sizes and lengths may be used to provide better fits and satisfy individual patients' needs. In total hip arthroplasty or total hip replacement operations, both the proximal femur and the acetabular surface are replaced and the entire hip implant 100 may be assembled during the surgery. In hemiarthroplasty, the acetabulum is left intact, while femoral head 115 and stem 120 are implanted during surgery. In particular, the natural femoral head is removed, the femoral canal is created, and femoral stem 120 is placed in the femoral canal, with or without the use of cement based on the patient's age and condition. Artificial femoral head or femoral ball 115 is then attached to a neck of femoral stem 120 with neck length appropriately adjusted for joint movement and equal leg length. In some embodiments, femoral stems made according to embodiments of the present invention may fit the standard femoral head and polyethylene insert, and may be directly used in standard surgical procedures. No additional orthopedic training or skills are required. In some embodiments, femoral stems made according to embodiments of the present invention may be used to replace failed conventional implants, without alternating the acetabular shell 105.

Figure 2:
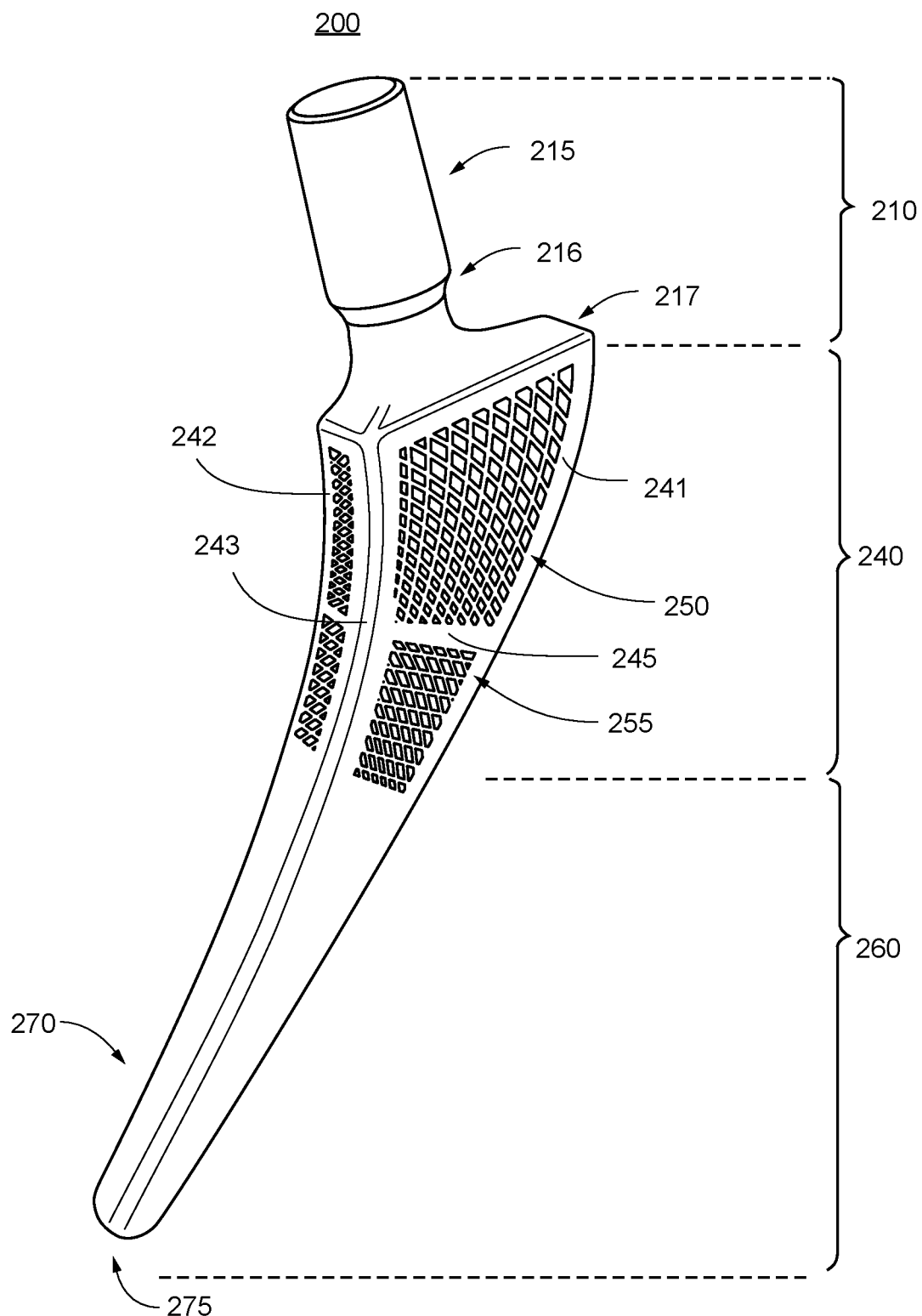
FIG. 2 is a perspective schematic diagram for a femoral stem design for a hip implant, according to one embodiment of the present invention.

FIG. 2 is a perspective schematic diagram of a femoral stem design 200 for a hip implant such as 100, according to one embodiment of the present invention. A rotated perspective view of the femoral stem 200 is shown in FIG. 2 for illustrative purposes. Femoral stem 200 comprises three main sections or portions, connected sequentially and extending in order from a proximal end to a lateral end of the femoral stem. The three main sections are femoral neck 210, upper body section 240, and lower body section 260.

In the exemplary embodiment shown in FIG. 2, femoral neck 210 is further divided into an elongated upper subsection 215, an optional middle transitional subsection 216, and an optional lower subsection 217. Upper subsection 215 is extended towards the acetabulum when implanted, shaped for compatibility with a standard femoral head, and may be contoured or configured to maximize the range of hip joint motion. A length of the upper subsection may be customized to ensure leg length equality and balanced hip muscle tension after surgery. Optional middle transitional subsection 216 is narrowed in diameter when compared to upper subsection 215, for secure locking into a femoral head. In addition, optional lower subsection 217 may be slightly tapered, having a wider base at the connection to upper body section 240, with the shape designed for controlling rotational stability and for reducing head-neck impingement during hip motion. In addition, in this embodiment, femoral neck 210 is collarless, with its bottom cross-section matching in size and shape the top cross-section of upper body 240.

Upper body section 240 and lower body section 260 are inserted into the femoral canal of the upper thigh during hip replacement therapy. In embodiments of the present invention, upper body 240 of femoral stem 200 comprises at least one solid proximal-distal rib, column, or post to enhance the overall bending strength and stiffness of femoral stem 200. More specifically, in this embodiment, four solid proximal-distal ribs including 241, 242, and 243 are present on the four corner edges to form a rectangular cage, tube, or cylinder, enclosing open lattice structures such as open lattices 250 and 255. In this embodiment, the proximal-distal solid ribs are pairs of parallel ribs, and each rib is contoured, curved, and shaped for best fitting into the femoral canal. In some embodiments, the proximal-distal solid ribs are straight columns. In some embodiments, each rib may be a narrow plate in the anterior-posterior direction. In some embodiments, at least one proximal-distal solid rib is selected from the group consisting of a plate in an anterior-posterior direction, a plate in a medial-lateral direction, and an intersection of two plates. In some embodiments, more than four proximal-distal solid ribs may be present.

In alternative embodiments, the proximal-distal solid ribs or rib reinforcements may have different shapes and locations, such as illustrated by FIGS. 3A and 9-11. The exact rib reinforcement design may be determined by structural analysis and biomechanical experiments based on patient information. Although not shown explicitly here in FIG. 2, it would be easy for persons of ordinary skills in the art to see that a transverse cross-section of upper body section 240 or lower body section 260 is non-circular. Instead, they may take on other rotationally stable or torsion resistant shapes such as trapezoids, quadrangles, or ellipses, which are also simple enough for progressive femoral medullary canal preparation, and are shown in FIG. 8 for illustrative purposes. The shape of the transverse cross-section of the hip implant matches that of the femoral canal.

As shown in FIG. 2, the proximal-distal ribs may be viewed as partially surrounded or flanked by one or more open lattice structures. In addition, upper section 240 may further comprise a solid transverse plate 245 that divides the open lattice structure into a first portion 250 and a second portion 255. Solid or semi-solid transverse plates and bars such as 245 further reinforce the stability of the femoral stem design, while also facilitating the manufacturing of two or more open lattices having different properties or configurations within upper section 240.

In the present disclosure, the term "open lattice" refers to a lattice structure without any external skin or shell, and which comes directly into contact with the bone canal or body tissues. A "closed lattice," on the other hand, refers to a lattice structure enclosed in some external skin or shell, which then in turn comes into contact with the bone canal or body tissues. Open lattices promote bone in-growth, while both lattice structures are lightweight with high strength.

In embodiments of the present invention, open lattice structures within upper body 240 accommodate bone in-growth and reduce the overall weight of the femoral stem to match the patient's natural bone density while maintaining a desired high structural strength. The osseointegration process facilitated by the porous lattice surface is of particular importance in securing the implant in the patient's proximal femur, allowing the implant to fuse with the patient's bone to provide a stable fixation, and to reduce or eliminate the use of cements, which may degrade over time, break off, and cause loosening of the implant.

Figure 15:
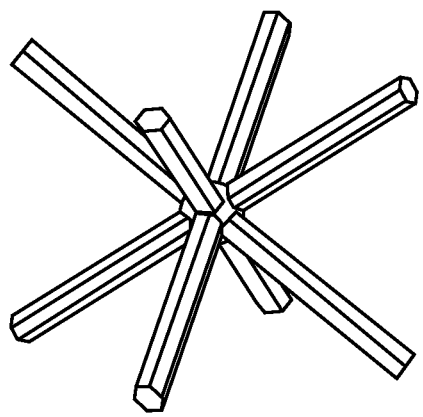
FIGS. 15, 16, and 17 are illustrative lattice structures for use in femoral stem designs, respectively, according to various embodiments of the present invention.
Figure 16:
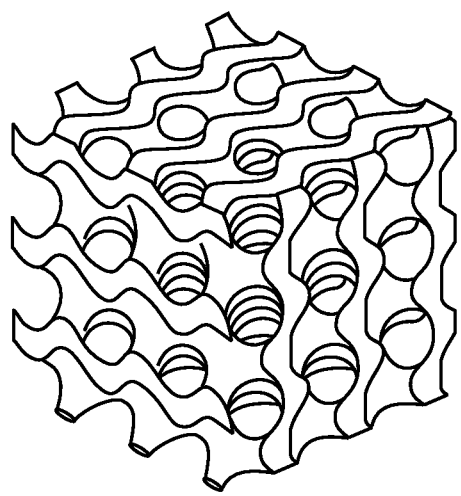
Figure 17:
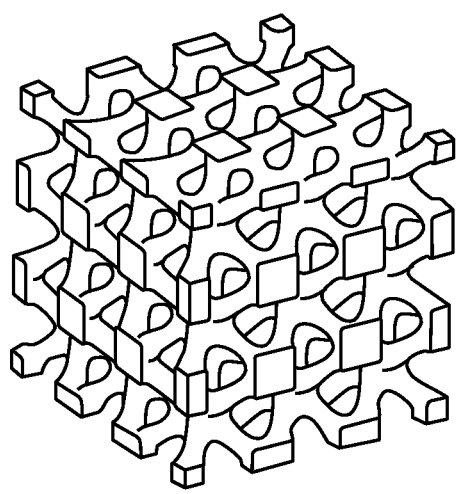

To maximize the biomechanical performance under stress and loading, and to promote bone in-growth, upper open lattice 250 and bottom open lattice 255 may contain different lattice structures in different embodiments of the present invention. The properties of the lattice structures such as topology, lattice structure or pore size distribution and density may be determined by structural analysis, simulation, and experiments, based on individual patient information and needs. Exemplary shapes for such lattice structures include, but are not limited to, square, triangular, trapezoidal, and hexagonal shapes, Voronoi patterns, organic shapes, hybrid of different type of shapes and many others. FIGS. 15-17 provide exemplary truss, gyroid lattice, and Schoen's I-WP lattice structures respectively. In various embodiments, one or more open lattice structures may surround, flank, or fill the space around or in-between one or more proximal-distal rib enforcements and transverse plates, where each lattice structure is characterized by a specific lattice topology, including lattice unit cell shape, size, and density. In some embodiments, one or more of the open lattice sections may be functionally graded, with varying gradient in porosity along a chosen axis. In some embodiments, some portions of the lattice structure in the upper body section may be closed.

In some embodiments, lower body 260 of femoral stem 200 may have a closed lattice interior (not shown explicitly in FIG. 2) comprising one or more different lattice structures, and enclosed in a solid exterior skin 270. When two or more lattice structures are present, an additional transverse plate may be present to separate the two, where the transverse plate may further comprise one or more escape holes for material removal during manufacturing. Lower body section 260 may be optimized in terms of skin thickness and lattice structure design to have lightweight and sufficiently large strength and stiffness.

In some embodiments of the present invention, a pore size of an open lattice within upper section 240 is smaller than a pore size of a closed lattice within lower section 260. In some embodiments, a pore size of each open lattice within upper section 240 is smaller than a pore size of each closed lattice within lower section 260. In some embodiments, a pore size of at least one open lattice in upper section 240 is between 0.1 mm inclusive and 2 mm inclusive. In some embodiments, a pore size of at least one open lattice in upper section 240 is between 0.1 mm inclusive and 5 mm inclusive. In some embodiments where more than one open lattice is present in upper body 240, a pore size of each open lattice in upper section 240 is between 0.1 mm inclusive and 5 mm inclusive. In some embodiments, a pore size of at least one closed lattice in lower section 260 is larger than or equal to 2 mm. In some embodiments where more than one close lattice is present in lower body 260, a pore size of each closed lattice in lower section 260 is larger than or equal to 2 mm.

In FIG. 2, a ratio in length between the upper and lower body sections is approximately 4:5. In different embodiments, the ratio in length between the upper and lower body sections may be between 0.25 inclusive to 4 inclusive.

In some embodiments, lower body 260 further comprises an escape hole located on a distal tip 275, and connected to a closed lattice within lower body section 260 for removing un-melted powder material during the manufacturing process, such as in EBM or SLM 3D printing processes. Easy power removal makes the femoral design especially suitable for Additive Manufacturing, which may utilize material such as titanium, chromium-cobalt, and stainless steel. Additive manufacturing refers to manufacturing technologies and processes for building from 3D design data three dimensional (3D) objects by "adding" or successively depositing layers-upon-layers of materials. The main advantage of additive manufacturing of medical implants over traditional casting approaches is it allows personalized customization based on individual patient's needs. In some embodiments, additional escape holes may be present on the solid skin of lower section 260 at different locations, and connected to the inner lattice for easy material removal.

In various embodiments of the present invention, the rib reinforcement in the upper body of the femoral stem assist in enhancing fatigue strength of the stem. The actual shape and location of the rib reinforcement might be different for different patients, which may be determined by structural analysis and biomechanical experiments. Having a multi-sectional design with different lattice structural topologies offers more flexibility to better accommodate loading conditions in motion and to maximize bone in-growth rate. Furthermore, the combination of open and closed lattices ensures optimal biomechanical performance of the resulting femoral stem. The open lattice structure within the upper body improves bone in-growth, while the closed lattice in the lower body enhances bending strength and minimizes the total weight of the femoral stem.

Figure 3A:
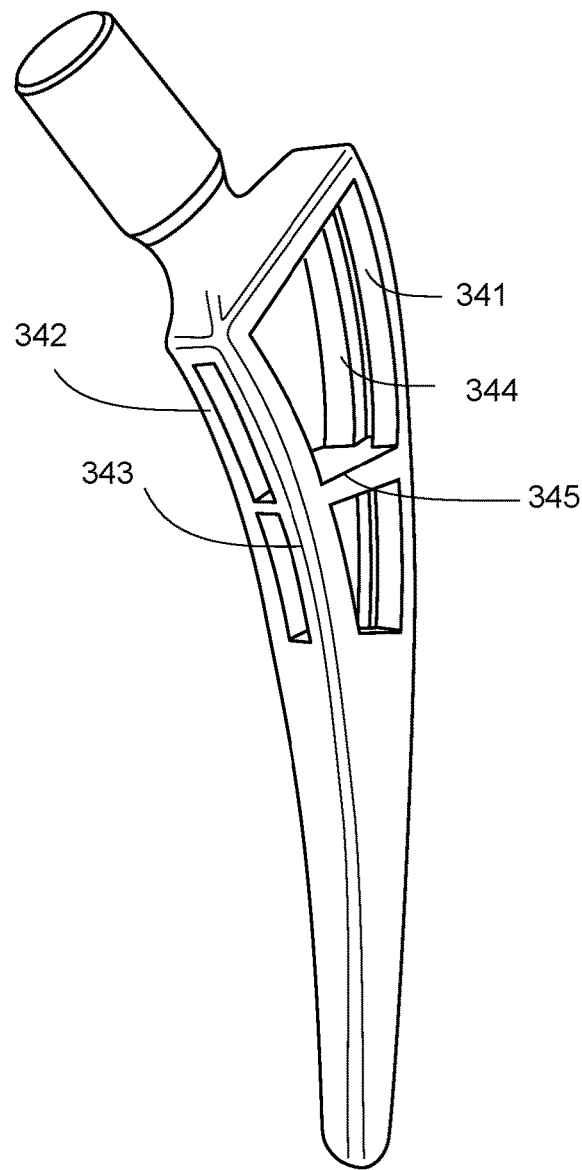
FIGS. 3A and 3B are two perspective views of the femoral stem shown in FIG. 2, respectively, illustrating proximal-distal solid ribs flanked by open lattice structures.
Figure 3B:
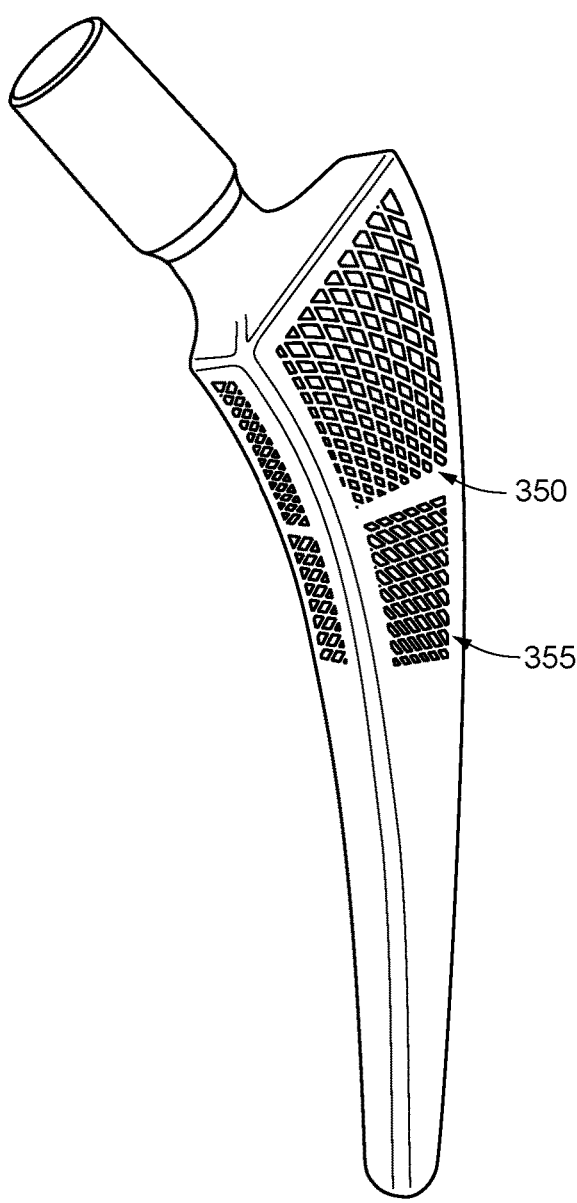

FIGS. 3A and 3B are two perspective views 300 and 350 of the femoral stem shown in FIG. 2, respectively, illustrating proximal-distal solid ribs flanked by open lattice structures. In FIG. 3A, four proximal-distal solid ribs 341, 342, 343, and 344 are shown, with a transverse plate 345 dividing the upper body section of the femoral stem into two separate portions. In FIG. 3B, the two separate portions are filled with open lattices 350 and 355. These two open lattices may have different designs or configurations to achieve desired femoral stem weight, density, stiffness, and strength.

FIGS. 4 and 5 are profile views 400 and 500 of two femoral stem designs for a hip implant respectively, illustrating different open lattices, according to some embodiments of the present invention. Lattice designs may be customized based on patient information.

Figure 6A:
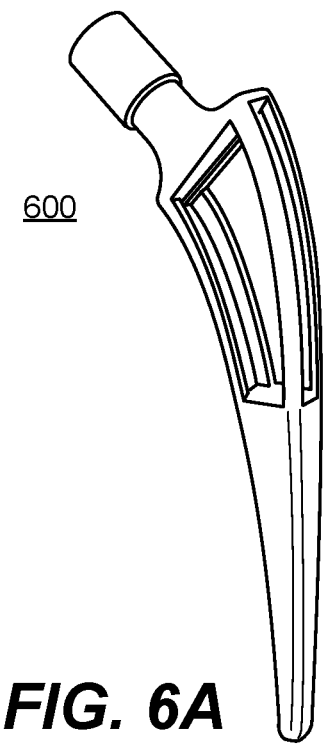
FIGS. 6A and 6B are schematic diagrams showing a femoral stem with rib reinforcements and an open lattice, respectively, according to several embodiments of the present invention.
Figure 6B:
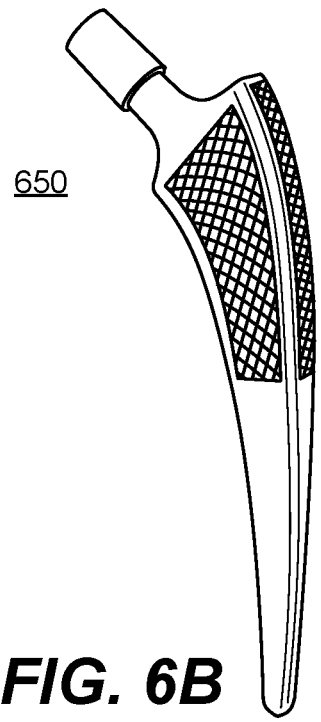
Figure 7A:
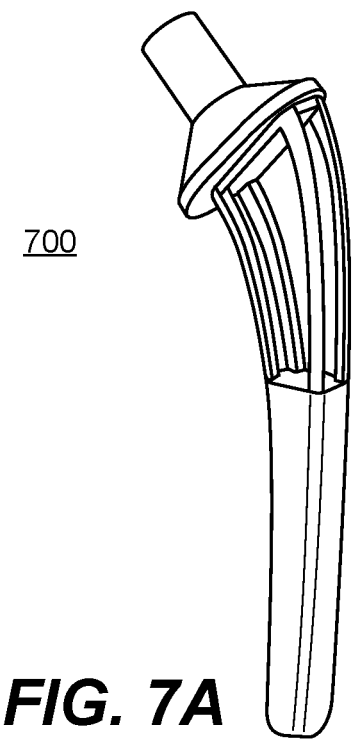
FIGS. 7A and 7B are schematic diagrams showing a collared femoral stem with rib reinforcements and an open lattice, respectively, according to several embodiments of the present invention.
Figure 7B:
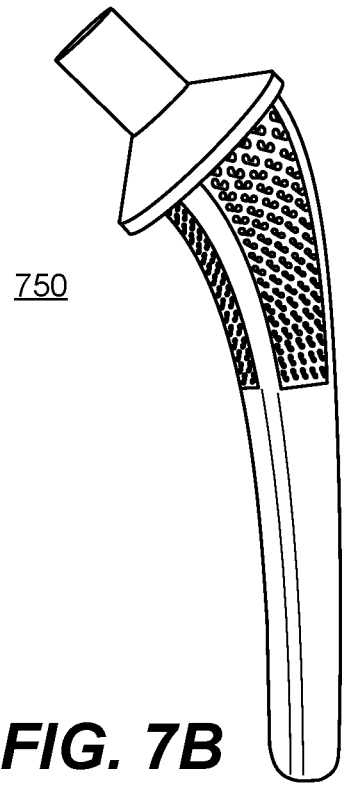

FIGS. 6A and 6B are schematic diagrams 600 and 650 showing a femoral stem with rib reinforcements and an open lattice, respectively, according to some embodiments of the present invention. FIGS. 7A and 7B are schematic diagrams 700 and 750 showing a collared femoral stem with rib reinforcements and an open lattice, respectively, according to some embodiments of the present invention. In FIGS. 6A and 7A, four proximal-distal ribs are present, to form a cage, which may be filled with open lattices. In addition, the femoral neck in FIGS. 6A and 6B is collar-less, while the femoral neck in FIGS. 7A and 7B are collared, where the bottom cross-section of the femoral neck is wider than the top cross-section of the upper body section. Many other proximal-distal rib designs are also possible, and may be personalized based on a patient's bone size, width, density, condition, body weight, and even activity levels. As disclosed previously, the ribs may be surrounded, flanked, or filled with open lattice structures.

FIG. 8 is a diagram showing illustrative transverse cross-sections of a femoral stem of a hip implant, according to several embodiments of the present invention. Such transverse cross-sections may be obtained by cross-sectioning the upper body section or the lower body section of a femoral stem, and they may take on rotationally stable or torsion resistant shapes such as trapezoids, quadrangles, or ellipses as shown, facilitating progressive femoral medullary canal preparation. The shape of the transverse cross-section of the hip implant matches that of the femoral canal. In addition, these cross-sectional views are meant to be illustrative and not limiting, and are not intended to limit the scope of the present invention. One of ordinary skill in the art would recognize that other cross-sections of the femoral stem are within the scope of the present invention.

Figure 9:
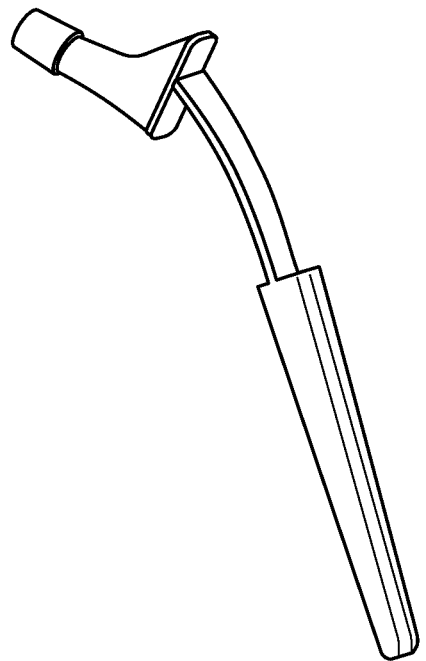
FIGS. 9, 10, and 11 are schematic diagrams showing femoral stems with different rib reinforcement designs, respectively, according to several embodiments of the present invention.
Figure 10:
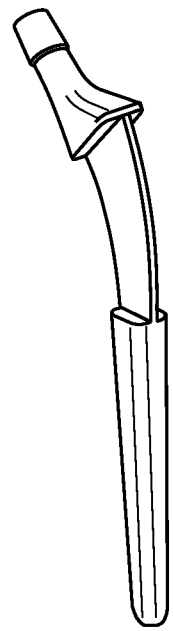
Figure 11:
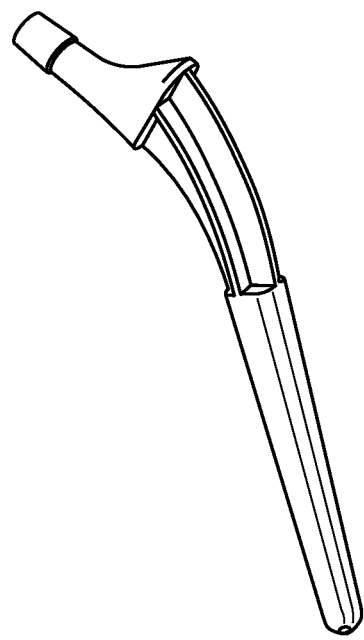

FIGS. 9, 10, and 11 are schematic diagrams showing femoral stems with different rib reinforcement designs, respectively, according to several embodiments of the present invention. In the embodiment shown in FIG. 9, the rib is a plate in the anterior-posterior direction. In the embodiment shown in FIG. 10, the rib is a plate in the mediolateral direction. In the embodiment shown in FIG. 11, the rib is a cross in the anterior-posterior and mediolateral directions.

Figure 12:
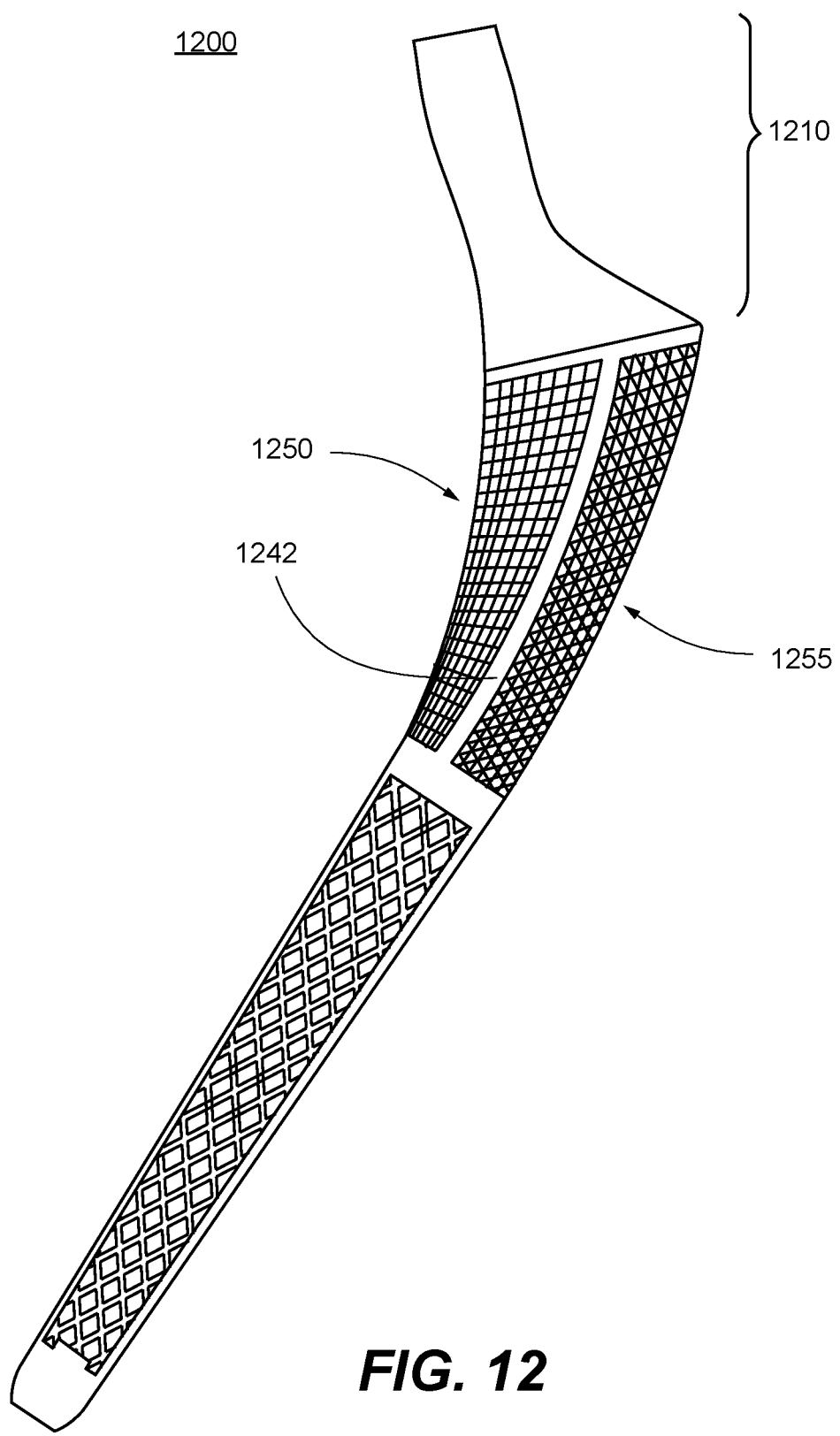
FIG. 12 is a longitudinal cross-section schematic diagram for another femoral stem design for a hip implant, according to one embodiment of the present invention.

FIG. 12 is a longitudinal cross-section schematic diagram 1200 for another femoral stem design for a hip implant, according to one embodiment of the present invention. In this embodiment, an anterior-posterior plate-shaped rib enforcement 1242 similar to that shown in FIG. 9 is flanked by a medial open lattice component 1250 and a lateral open lattice component 1255. In addition, a femoral neck 1210 of this femoral stem comprises a tapered but collarless, solid bottom portion for connecting with an upper body section of the femoral stem.

Figure 13:
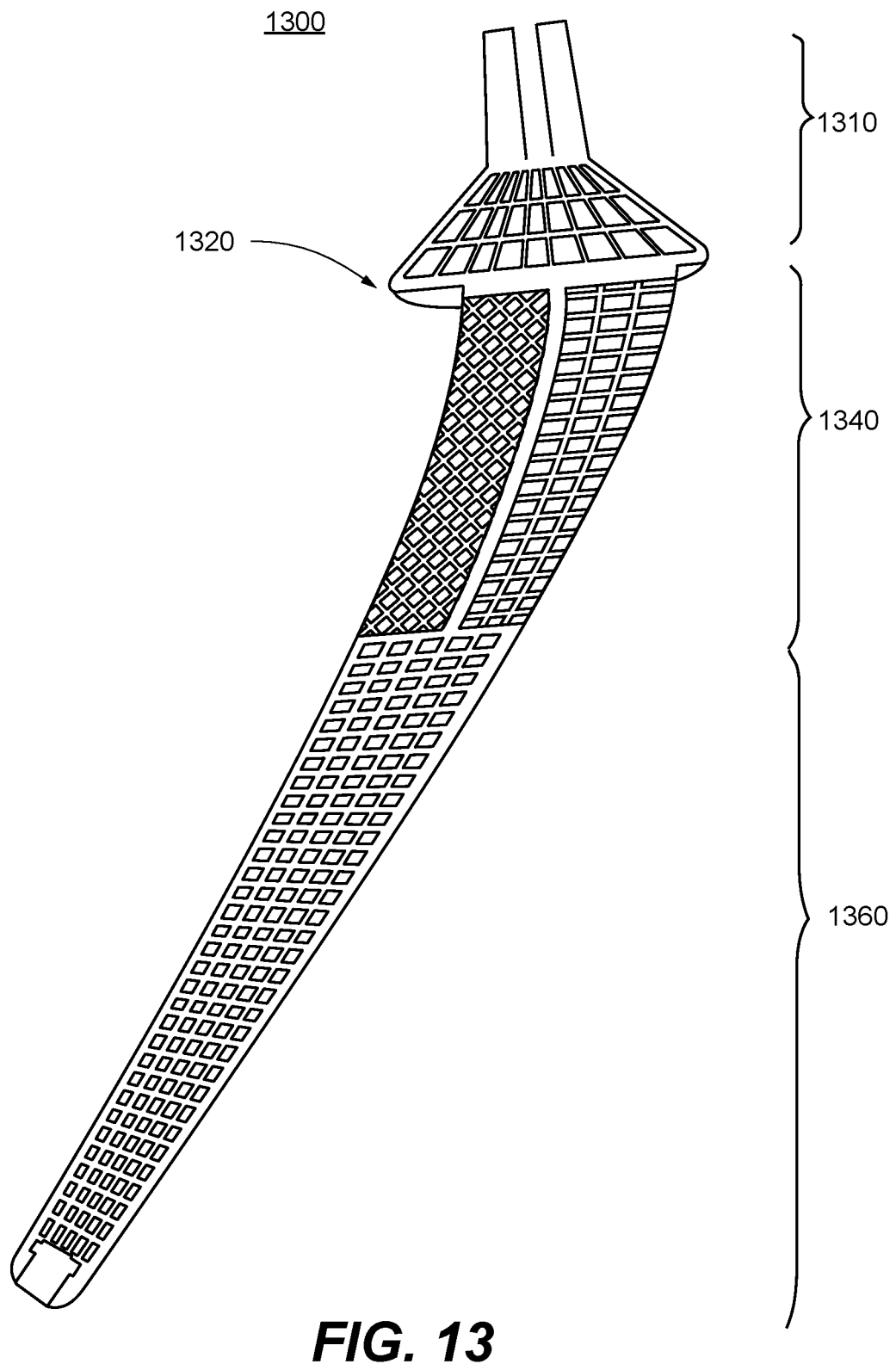
FIG. 13 is a longitudinal cross-section schematic diagram for a collared femoral stem design for a hip implant, according to one embodiment of the present invention.

FIG. 13 is a longitudinal cross-section schematic diagram 1300 for a collared femoral stem design for a hip implant, according to one embodiment of the present invention. In this embodiment, femoral neck 1310 comprises a closed lattice and an escape hole at a top of the femoral neck, and has a "collar" or bottom 1320 that is wider than the transverse cross-section of the upper body of the stem. Thus, the interior of part or all of femoral neck 1310 is filled with a lattice structure, optimized to have light weight but sufficiently large stiffness and strength. A collared femoral neck assists in avoiding subsidence and adds rotation stability, especially in older patients with osteopenia or osteoporosis. In addition, upper body section 1340 comprises a proximal-distal rib surround by open lattice structures, while lower body section 1360 comprises a closed lattice enclosed in a solid exterior and an escape hole.

Figure 14A:
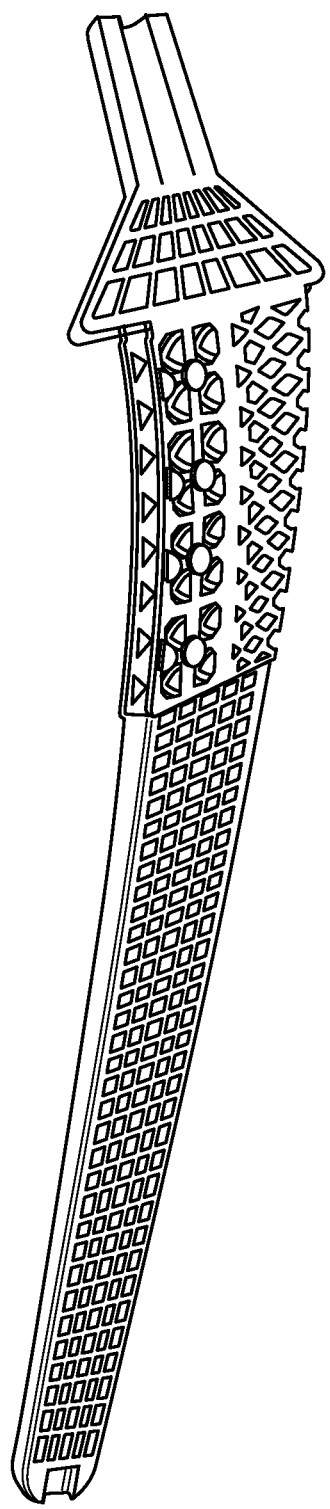
FIG. 14A is a longitudinal cross-section view of a femoral stem prototype made based to the design shown in FIG. 13.
Figure 14B:
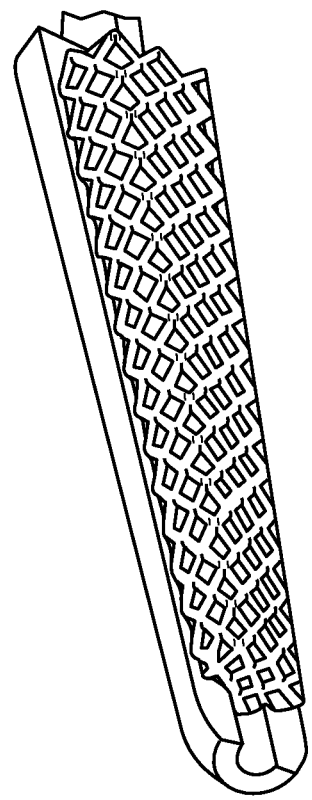
FIG. 14B is a schematic view of a lower inner body of the femoral stem design shown in FIG. 13, according to one embodiment of the present invention.

Corresponding to FIG. 13, FIG. 14A is another rotated longitudinal cross-section view of a femoral stem prototype, according to some embodiments of the present invention. FIG. 14B is a schematic view of a lower inner body of the femoral stem, showing the inner lattice structure partially without the exterior skin and an escape hole on the distal end of the femoral stem. In this particular embodiment, different lattice unit cells are utilized in different parts of the femoral stem.

FIGS. 15, 16, and 17 are illustrative lattice structures for use in femoral stem designs, respectively according to various embodiments of the present invention. In particular, FIG. 15 shows a truss lattice, FIG. 16 shows a gyroid lattice, and FIG. 17 shows a Schoen's I-WP lattice. These different types of lattices provide different ranges of pore sizes and mechanical properties. The truss lattice in FIG. 15 has a larger range of pore sizes to adjust, and is most suitable for reducing weight, and may be a good choice for use in closed lattice. While gyroid lattice in FIG. 16 and Schoen's I-WP lattice in FIG. 17 have smaller ranges of pore size to adjust, these two lattices have better mechanical properties and are stronger than the truss lattice. These lattice structures shown here are illustrative of selected embodiments of the present invention, and the present invention is not limited to the lattice structures shown here. One of ordinary skill in the art would recognize that other lattice structures are also within the scope of the present invention.

For the various embodiments of the present invention disclosed so far, loading simulation models may be analyzed, with same loading and boundary condition setting used for different femoral stem designs, with or without rib enforcements and/or open lattice structures. Lattices with rib designs have lower tensile stresses than that without rib reinforcements. Since fatigue strength is directly related to tensile stress, lower stress means more fatigue life.

Figure 18:
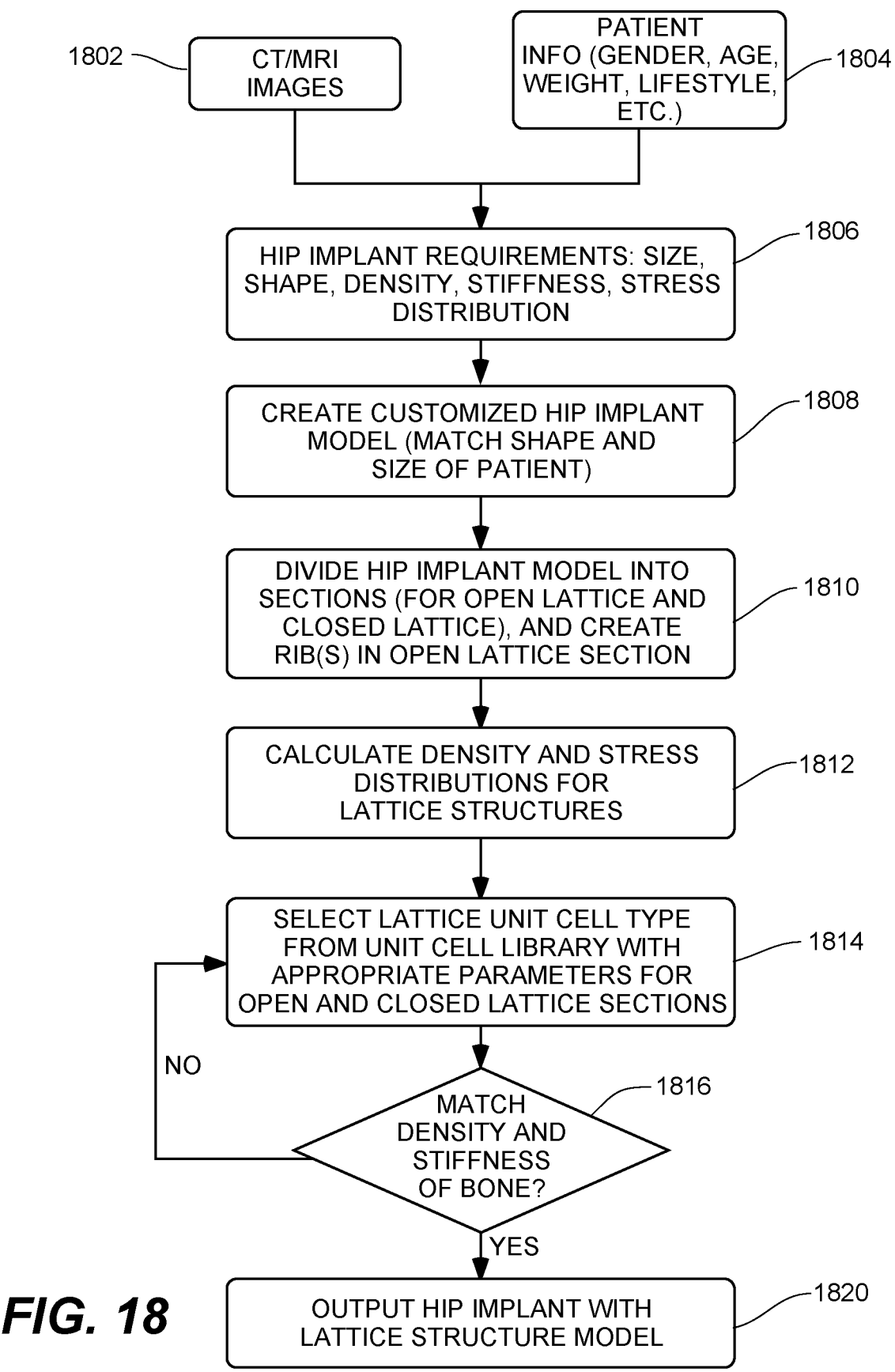
FIG. 18 is a flowchart for an illustrative process to generate a customized femoral stem of a hip implant, according to one embodiment of the present invention.

FIG. 18 is a flowchart for an illustrative process to generate a customized femoral stem of a hip implant, according to one embodiment of the present invention. In short, the process comprises the steps of creating a customized femoral stem model to match the bone shape and size of a patient, wherein the hip implant model comprises a femoral neck portion, an upper body portion, and a lower body portion; creating one or more proximal-distal solid ribs in the upper body portion; calculating density and stress distributions for an open lattice structure surrounding the one or more proximal-distal solid ribs; and selecting a lattice unit cell type for the open lattice structure to match the density and/or stiffness of the patient's femur.

More specifically, as a first step of implant customization, CT and/or MRI images 1802 of the patient's hip joint and proximal femur may be obtained preoperatively, as well as other patient information 1804 including gender, age, weight, lifestyle, etc. A set of hip implant design requirement or specification may then be calculated or estimated in Step 1806, including desired implant size, shape, density, stiffness, and stress distribution. A customized hip implant or femoral stem model may then be created in Step 1808 to match the shape and size of the patient. This hip implant model may be divided into upper and lower sections in Step 1810, with open and closed lattice structures, and one or more ribs for reinforcement in the upper section may be added with open lattice structures. Next, density and stress distributions for the lattice structures are calculated in Step 1812. A lattice unit cell type may be selected from a unit cell library with appropriate parameters for the open and closed lattice sections in Step 1814, and the resulting implant density and stiffness matched to that of the patient's bone in Step 1816. Different lattice unit cell types may be tested until a satisfying match is found, and the resulting design may be outputted both visually and mathematically in Step 1820, for use with 3D printing machines and systems.

Figure 19:
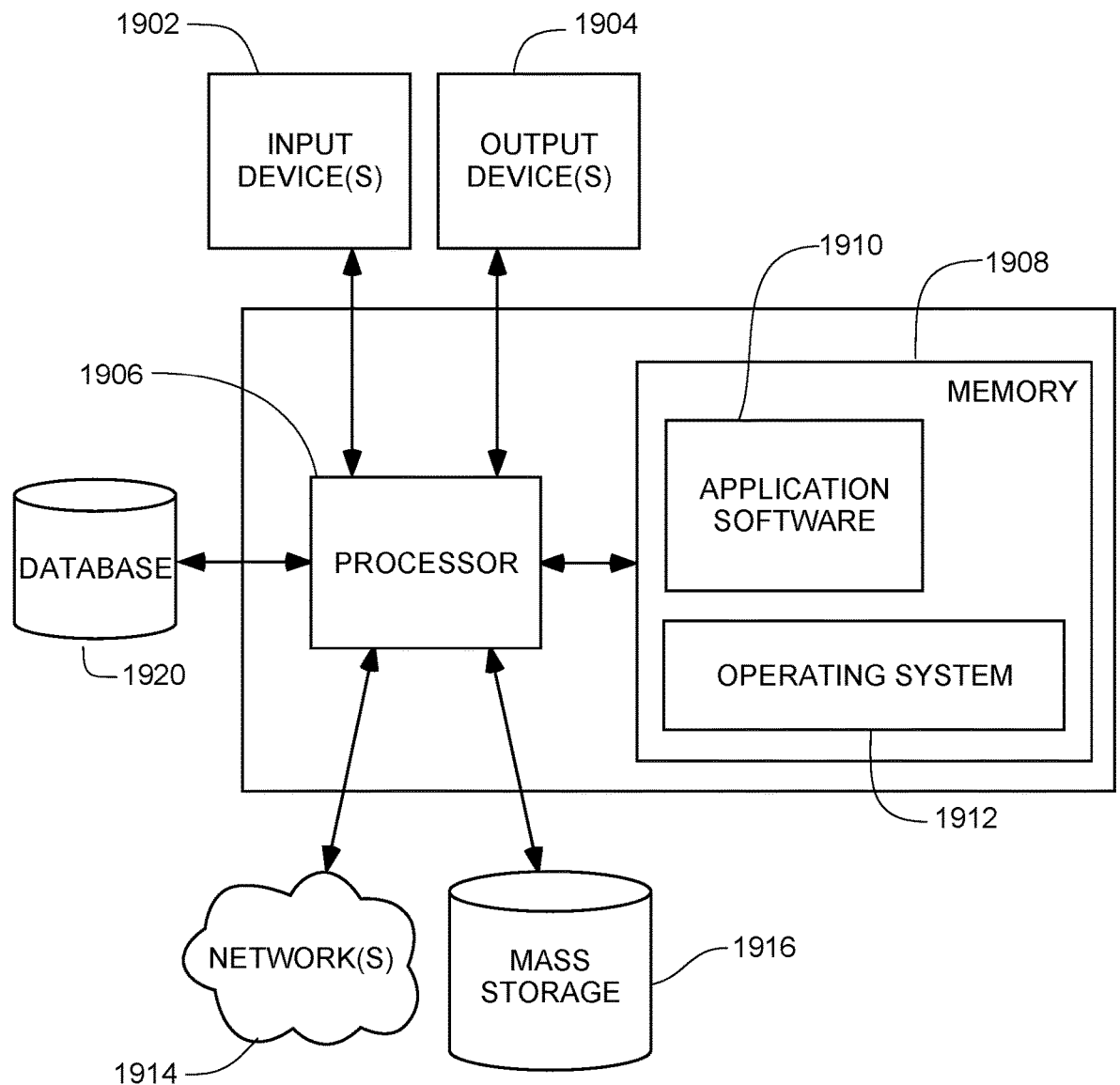
FIG. 19 is an illustrative hardware architecture diagram of a system for implementing embodiments of the present invention.

The design process illustrated by FIG. 18 may be implemented using server-based hardware and software. For example, FIG. 19 is an illustrative architecture diagram of a system for implementing embodiments of the present invention. Many components of the system, for example, network interfaces etc., have not been shown, so as not to obscure the present invention. However, one of ordinary skill in the art would appreciate that the system may include these components. In FIG. 19, a processor-based computing device is shown, which includes at least one processor 1906 coupled to a memory 1908. Processor 1906 may represent one or more processors (e.g., microprocessors), and memory 1908 may represent random access memory (RAM) devices comprising a main storage of the hardware, as well as any supplemental levels of memory e.g., cache memories, non-volatile or back-up memories (e.g. programmable or flash memories), read-only memories, etc. In addition, memory 1908 may be considered to include memory storage physically located elsewhere in the hardware, e.g. any cache memory in the processor, as well as any storage capacity used as a virtual memory, e.g., as stored on a mass storage device.

The hardware of the computing device may receive a number of inputs including patient information or design specification via one or more input devices 1902 or internal/external databases 1920, and output the design result through one or more output devices 1904. For example, to interface with a user such as an operating designer or a surgeon, the hardware may include one or more user input devices (e.g., a keyboard, a mouse, a scanner, a microphone, a web camera, etc.) and a display (e.g., a Liquid Crystal Display (LCD) panel). The illustrating computing device may also be directly connected to an Additive Manufacturing device for constructing a prototype or a finalized hip implant design. For additional storage, the hardware my also include one or more mass storage devices 1916, e.g., a floppy or other removable disk drive, a hard disk drive, a Direct Access Storage Device (DASD), an optical drive (e.g. a Compact Disk (CD) drive, a Digital Versatile Disk (DVD) drive, etc.) and/or a tape drive, among others. Furthermore, the hardware may include an interface one or more external databases, as well as one or more networks 1914 (e.g., a local area network (LAN), a wide area network (WAN), a wireless network, and/or the Internet among others) to permit the communication of information with other computers coupled to the networks. It should be appreciated that the hardware typically includes suitable analog and/or digital interfaces to communicate with each other.

The hardware operates under the control of an operating system, and executes various computer software applications, components, programs, codes, libraries, objects, modules, etc. indicated collectively by reference numerals to perform the methods, processes, and techniques described above.

In general, the method executed to implement the embodiments of the invention, may be implemented as part of an operating system or a specific application, component, program, object, module or sequence of instructions referred to as "computer program(s)" or "computer code(s)." The computer programs typically comprise one or more instructions set at various times in various memory and storage devices in a computer, and that, when read and executed by one or more processors in a computer, cause the computer to perform operations necessary to execute elements involving the various aspects of the invention. Moreover, while the invention has been described in the context of fully functioning computers and computer systems, those skilled in the art will appreciate that the various embodiments of the invention are capable of being distributed as a program product in a variety of forms, and that the invention applies equally regardless of the particular type of machine or computer-readable media used to actually effect the distribution. Examples of computer-readable media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), and digital and analog communication media.

In some embodiments of the present invention, the entire system can be implemented and offered to end-users and operators over the Internet, in a so-called cloud implementation. No local installation of software or hardware would be needed, and the end-users and operators would be allowed access to the systems of the present invention directly over the Internet, using either a web browser or similar software on a client, which client could be a desktop, laptop, mobile device, and so on. This eliminates any need for custom hardware or software installation on the client side and increases the flexibility of delivery of the service (design-as-a-service), and reduced the cost of dedicated Additive Manufacturing hardware.

One of ordinary skill in the art knows that the use cases, structures, schematics, and diagrams may be constructed or performed in other combinations or orders, but the inventive concept of the present invention remains without departing from the broader scope of the invention. Every embodiment may be unique, and constituting components may be either shortened or lengthened, narrowed or widened; methods and steps may also be shortened or lengthened, overlapped with other activities, postponed, delayed, and continued after a time gap, during the practice of the present invention.

Although the present invention has been described with reference to specific exemplary embodiments, it will be evident that the various modification and changes can be made to these embodiments without departing from the broader scope of the invention. Accordingly, the specification and drawings are to be regarded in an illustrative sense rather than in a restrictive sense. It will also be apparent to the skilled artisan that the embodiments described above are specific examples of a single broader invention which may have greater scope than any of the singular descriptions taught. There may be many alterations made in the descriptions without departing from the scope of the present invention as defined by the appended claims.

What is claimed is:

1. A method of manufacturing a femoral stem for a hip implant, comprising:
    forming a femoral neck extending from a proximal end of the femoral stem towards a distal end of the femoral stem;
    forming an upper section connected to and extending from the femoral neck towards the distal end of the femoral stem, wherein the upper section comprises at least one proximal distal solid rib flanked by an open lattice, wherein the upper section further comprises a transverse plate, wherein the transverse plate divides the open lattice into a first portion and a second portion, and wherein the first portion and the second portion are different in at least one of a unit cell type and a pore size; and
    forming a lower section connected to and extending from the upper section towards the distal end of the femoral stem, wherein the lower section comprises a closed lattice enclosed in a solid skin.

2. The method of claim 1, wherein the at least one solid rib comprises four or more proximal-distal solid ribs.

3. The method of claim 1, wherein a pore size of the open lattice is smaller than a pore size of the closed lattice.

4. A method for designing a femoral stem for a hip implant, comprising:
    generating a customized femoral stem model to match an information of a patient, wherein the femoral stem model comprises a femoral neck extending from a proximal end of the femoral stem towards a distal end of the femoral stem, an upper section connected to and extending from the femoral neck towards the distal end of the femoral stem, and a lower section connected to and extending from the upper section towards the distal end of the femoral stem, the upper section comprising an open lattice, and the lower section comprising a closed lattice enclosed in a solid skin, wherein the upper section further comprises a transverse plate, wherein the transverse plate divides the open lattice into a first portion and a second portion, and wherein the first portion and the second portion are different in at least one of a unit cell type and a pore size;
    generating at least one proximal distal solid rib in the upper section;
    calculating density and stress distributions for the open lattice flanking the at least one proximal distal solid rib in the upper section, and for the closed lattice in the lower section; and
    selecting a first lattice unit cell type and a first pore size for the open lattice and a second lattice unit cell type and a second pore size for the closed lattice to match a density and/or a stiffness of the patient's femur.

5. The method of claim 4, wherein the information of the patient comprises at least one of a femur shape, a size, a density, and a stiffness.

6. The method of claim 4, wherein the at least one solid rib comprises four or more proximal-distal solid ribs.

7. The method of claim 4, wherein the first pore size of the open lattice is smaller than the second pore size of the closed lattice.

* * * * *